United States Patent [19]

Hersh et al.

[11] Patent Number: 4,807,631
[45] Date of Patent: Feb. 28, 1989

[54] PULSE OXIMETRY SYSTEM

[75] Inventors: Lawrence T. Hersh, Tampa; Richard Medero, Clearwater; Rush W. Hood, Jr., Tampa, all of Fla.

[73] Assignee: Critikon, Inc., Tampa, Fla.

[21] Appl. No.: 107,138

[22] Filed: Oct. 9, 1987

[51] Int. Cl.$^4$ ............................................... A61B 5/00
[52] U.S. Cl. .................................... 128/633; 128/666; 356/41
[58] Field of Search .................... 128/633, 666; 356/41

[56] References Cited

U.S. PATENT DOCUMENTS

| | | | |
|---|---|---|---|
| 3,647,299 | 3/1972 | Lavallee | 128/633 X |
| 4,266,554 | 5/1981 | Hamaquri | 356/41 X |
| 4,407,290 | 10/1983 | Wilber | 128/633 |
| 4,653,498 | 3/1987 | New, Jr. et al. | 128/633 |
| 4,694,833 | 9/1987 | Hamaquri | 128/633 |
| 4,714,080 | 12/1987 | Edgar, Jr. et al. | 128/633 |

Primary Examiner—Lloyd L. King

[57] ABSTRACT

A pulse oximetry system is provided in which LEDs of two different wavelengths illuminate tissue containing arterial blood flow. A photodiode receives light from the LEDs and produces electrical signals containing pulsatile components. The components of the two wavelengths are separated and the pulsatile waveforms are monitored until signal peaks are detected at the end of diastole. The waveforms are then integrated over the systolic interval, and the integrals are combined with the signal peak values to determine an index value. The index value is used to select a value representative of oxygen saturation from a look-up table.

18 Claims, 4 Drawing Sheets

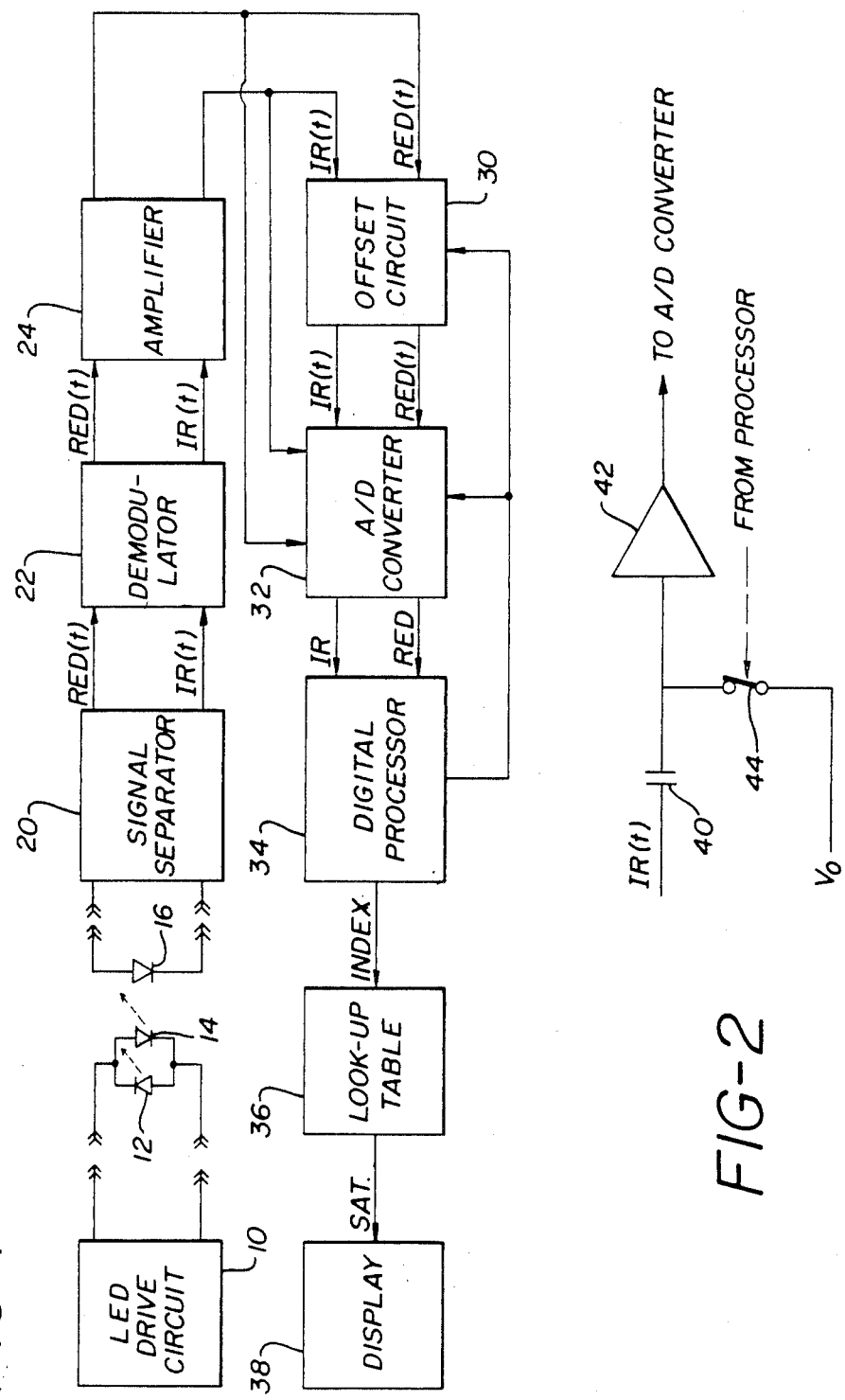

PULSE OXIMETRY SYSTEM

This invention relates to oximeter systems and, in particular, to a pulse oximetry system for measuring the oxygen content of arterial blood.

Pulse oximetry is a non-invasive medical technique useful for measuring certain vascular conditions. In practice of the technique, light is passed through a portion of a patient's body which contains arterial blood flow. An optical sensor is used to detect the light which has passed through the body, and variations in the detected light at various wavelengths are then used to determine arterial oxygen saturation and/or pulse rates. Oxygen saturation may be calculated using some form of the classical absorption equation known as Beer's Law.

In prior art oximeter systems, electrical signals are produced which are representative of the transmissions of two wavelengths of light through tissue where arterial blood flow is present. These signals are strongly dominated by a substantially constant component, with the component representative of pulsatile blood flow being a much smaller component. The received signal is normalized by dividing it by an average signal level, sometimes referred to as a DC component. The normalization is performed on signals of both wavelengths to produce comparably scaled signal samples.

After normalization the samples are often then converted to logarithmic values and then used to calculate oxygen saturation. The formulae used to calculate oxygen saturation are generally in the form of a quotient of series expansions of terms. These computations are often complex, time-consuming in their execution, and require substantial computational capability.

In accordance with the principles of the present invention, a simple yet accurate pulse oximetry system is provided. Received analog signals from the transmission of two wavelengths of light are controllably offset so as to occupy a substantial portion of the dynamic range of an analog-to-digital (A/D) converter. The signals are then respectively monitored until the end of diastole is detected. The signal level at the end of diastole is used as a reference value in conjunction with the signals occurring during systole. The sequence of samples occurring during systole are used to compute an integral of each signal waveform over the systolic interval and the integral values are then divided by the corresponding reference value. At the end of systole the two terms so computed for the respective wavelengths of light are used to form a quotient of the two terms. This quotient is an index value, used to access a look-up table, whereby the level of oxygen saturation is read out and displayed. The terms forming the quotient effectively represent the integral of each optical waveform taken over systole, and divided by the signal level at the transmission between diastole and systole.

In the drawings:

FIG. 1 illustrates in block diagram form a pulse oximeter constructed in accordance with the principles of the present invention;

FIG. 2 illustrates schematically a circuit used to emphasize the pulsatile signal waveform;

Figure 3:
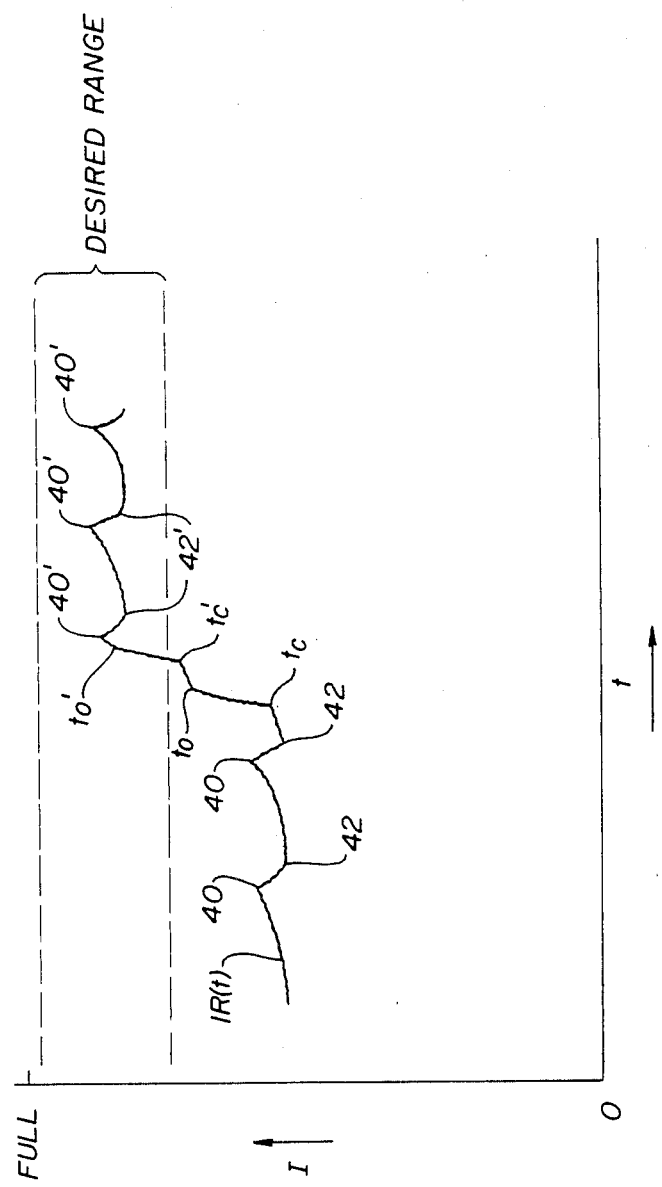
Figure 4:
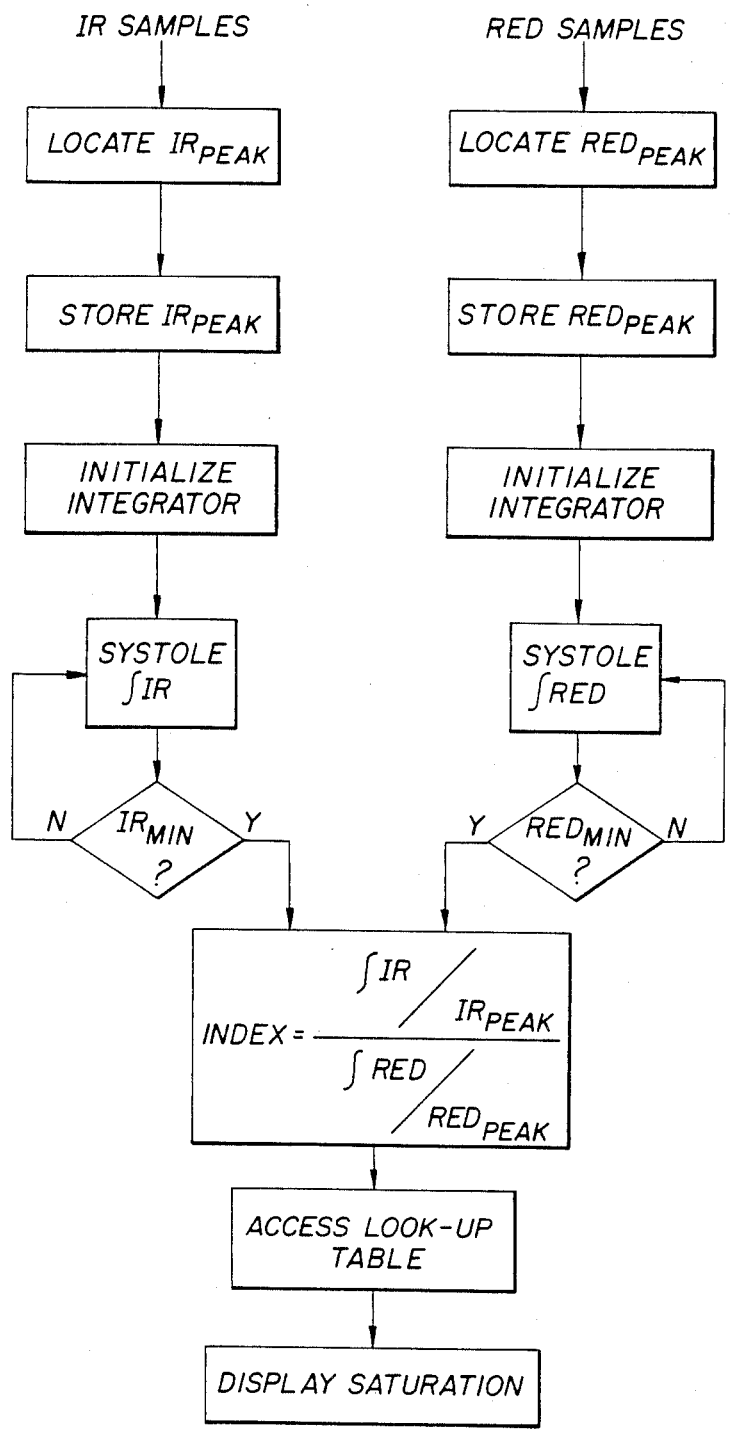
Figure 5:
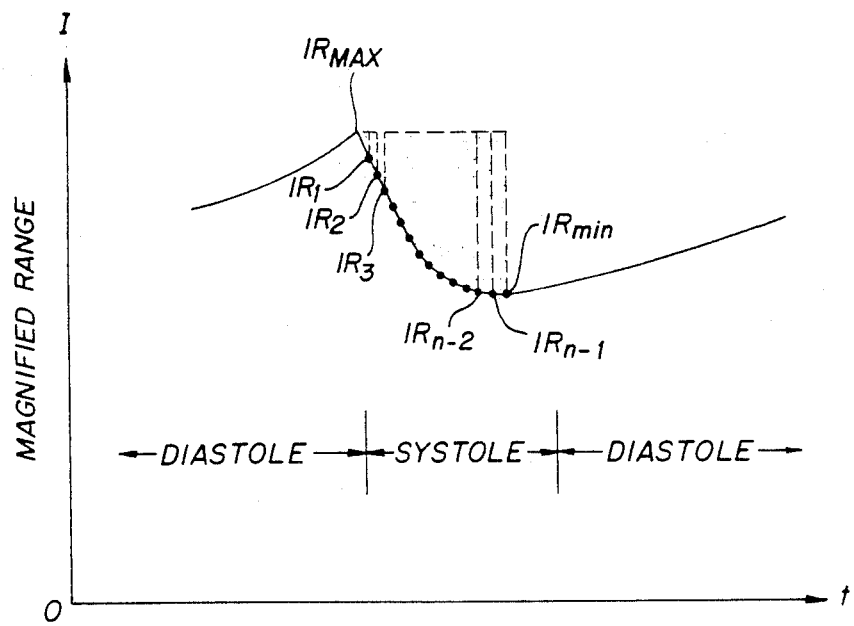

FIG. 3 graphically illustrates operation of the circuit of FIG. 2;

FIG. 4 is a flowchart of a computer program used to determine oxygen saturation; and FIG. 5 graphically illustrates the operation of the computer program of FIG. 4.

Referring first to FIG. 1, a pulse oximetry system constructed in accordance with the principles of the present invention is shown. Two light emitting diodes (LEDS) 12 and 14 are connected by a suitable connector to a drive circuit 10, which alternately energizes the LEDs. The LEDs transmit light at two predetermined wavelengths, referred to herein as red and infrared (IR), through tissue containing a flow of arterial blood. The transmitted light, which has been affected by the pulsatile blood flow, is received by a photodiode 16. The photodiode converts the received optical signals to electrical signals, which are coupled by a suitable connector to a signal separator 20. The signal separator 20 separates the red and IR signal components, which are then detected by an amplitude demodulator 22. Circuitry for performing these functions is more particularly described in U.S. patent application No., filed Oct. 8, 1987 and entitled "PULSE OXIMETER PLETHYSMOGRAPH SYSTEM".

The separated red and IR signals are amplified by an amplifier 24 and coupled to an offset circuit 30. The offset circuit 30 controllably shifts the red and IR signal levels so that they occupy a significant portion of the input dynamic range of an A/D converter 32. The A/D converter 32 digitizes the offset and unoffset red and IR signals, which are then coupled to a digital processor 34. The digital processor 34, in a manner to be more fully described hereinafter, monitors the successive signal samples until the onset of systole is detected. The signal peak at the transition from diastole to systole is stored, and an integration of each signal waveform over systole is performed. Each integral is divided by its respective stored peak signal level, and the two resulting terms are used to form a quotient, referred to as an index value. The index value represents a highly resolved measurement of the degree of oxygen saturation of the arterial blood flow. The index value is used to access a corresponding oxygen saturation value in a look-up table 36, and this value is displayed on a display 38 as the percent of oxygen saturation.

The offset circuit 30 is schematically represented in FIG. 2. Two such circuits are provided, one for the red signal and one for the IR signal; the circuit for the IR signal is shown in FIG. 2, which is identical to the circuit for the red signal. In FIG. 2, the IR signal is capacitively coupled by a capacitor 40 to the input of a high impedance amplifier 42, such as an FET amplifier. At the junction of the capacitor 40 and the input to the amplifier 42 is a switch 44. The switch 44 is controllably opened and closed by the digital processor 34 to selectively charge capacitor 40 from an offset voltage source Vo. The amplified signals produced by the amplifier 42 are coupled to the A/D converter 32.

The effect of the offset circuit is to "magnify" the pulsatile component of the received optical signal. The circuit does this by shifting the signal to an appropriate predetermined level, at which it is amplified to occupy a substantial portion of the dynamic input range of the A/D converter. FIG. 3 explains how this shifting takes place. In the example of FIG. 3, the time-varying pulsatile IR signal component IR(t) is initially seen to be in the center of a range extending from zero to "full". This is the signal appearing at the junction of the capacitor 40, the switch 44, and the amplifier 42. At the end of diastole the IR(t) signal reaches peaks shown at 40. The signal level drops during systole to the levels indicated as 42, whereafter the signal rises again during diastole to the level of 40. In this example it is desired to increase the peaks 40 so that they are near the "full" range level. Subsequent amplification of the signal at this level will cause it to occupy a substantial portion of the input range of the A/D converter.

The first few cycles of the IR(t) signal represent the signal condition when the switch 44 is open. At this time the capacitor 40 has a constant charge, and couples the IR(t) signal to the amplifier. The degree of offset is established by the charge on the capacitor. The digital processor will sense that the signal level is too low, and at time $t_c$ the switch 44 is closed. The right plate of the capacitor 40 is now charged by current from the offset voltage source $V_o$, causing the signal level to rapidly rise. At time $t_o$ the switch 44 is opened, and the charge on the capacitor remains constant. The input to amplifier 42 follows the IR(t) signal, but at a higher level. At times $t_{c'}$ and $t_{o'}$ the switch 44 is closed and opened once more, shifting the signal level higher yet. After time $t_{o'}$ the signal at the input of amplifier 42 continues to follow the IR(t) signal until the peak at the end of diastole is reached as shown at 40'. The shifted IR(t) signal continues at this new level within the "magnified" desired range until deteriorated by current leakage, which is minimized by the high input impedance of amplifier 42. Should the IR(t) signal level drift outside the desired range due to leakage, the switch 44 is again periodically closed during diastole to again shift the signal. The offset circuit will always drive the signal to a level within the desired range, which is determined by the choice of offset voltage $V_o$. In the preferred embodiment of the present invention it is important to shift the signal only during diastole, as measurements are taken during systole as described below.

The digital processor 34 is responsive to sampled values of the IR(t) and Red(t) signals to produce an index value representative of oxygen saturation. The digital processor in a preferred embodiment executes a computer program illustrated by the flowchart of FIG. 4. Samples of the IR(t) and Red(t) signals are continuously monitored until the signal peaks of the unoffset signals at the transition between diastole and ystole are detected. This may be done by continuously calculating the slope of the waveform and looking for the inflection point. In the preferred embodiment the signal peaks $IR_{peak}$ and $RED_{peak}$ are located by calculating the derivatives of the respective signal waveforms. These peak values are stored and integrators of the signal waveforms are initialized. The integrators of the respective waveforms then integrate each offset signal during systole. The integration reduces noise effects, and is performed on the "magnified" (offset) signal for maximum resolution. The end of systole is indicated by the next inflection point of the signal waveform, or a sign change of the derivative function.

The integral functions, $\int IR$ and $\int RED$, each performed over the systolic interval, are then combined to compute an index value. The $\int IR$ function is divided by the stored $IR_{peak}$ value and the $\int RED$ function is divided by the stored $RED_{peak}$ value. The divided functions are combined in a quotient, which defines the index value. The index value is then used to access the look-up table 36 where the corresponding value of oxygen saturation is found and displayed.

The look-up table may be generated empirically by applying the LEDs and photodiode to tissue samples of known levels of oxygen saturation. As the level of oxygen saturation is changed the corresponding index values are noted, and oxygen saturation values are stored in the look-up table in correspondence to the index values.

Referring to FIG. 5, the operation of the computer program of FIG. 4 is graphically illustrated. The offset IR(t) waveform is seen to attain its peak value, $IR_{max}$, at the end of the diastole. (The RED(t) waveform has a similar shape and attains its peak value $RED_{max}$ at the same time. Hence discussion of the IR signal is sufficient to describe both.) Once $IR_{max}$ (or $IR_{peak}$) has been attained, the integrator begins to integrate the waveform during systole. The amplitude between each successive value $IR_1$, $IR_2$, ... $IR_{n-1}$, $IR_{min}$, taken at its respective point in time, and the $IR_{max}$ level, defines the waveform integral which is shown as a stippled area in FIG. 5. When the waveform reaches its minimum value at $IR_{min}$, the end of systole, the integration of the waveform ends. Thereafter, the waveform again rises during the next diastolic interval. Because the system does not use the information during diastole for integral calculations, it is during this period that the digital processor may activate the offset circuit to reposition the signal level.

It has been found that the index values calculated as illustrated herein provide sufficient resolution for an accurate indication of oxygen saturation.

What is claimed is:

1. An oximetry system for measuring blood oxygen saturation comprising:
    means for illuminating tissue containing arterial blood with light of two different wavelengths;
    means for receiving light from said illuminating means and producing corresponding electrical signals of said two wavelengths of light;
    means for measuring the peaks of said signals at the transition of the illuminated blood from diastole to systole;
    means for integrating said signal waveforms during systole to produce integral values;
    means for combining said integral values and signal peaks to determine an index value; and
    means responsive to said index value for producing an indication of oxygen saturation of the arterial blood.

2. The oximetry system of claim 1, wherein said receiving means includes
    means, responsive to said received light, for producing separated signal components representative of light of two different wavelengths.

3. The oximetry system of claim 2, wherein said receiving means further includes demodulator means responsive to said separated signal components for producing electrical signals of two wavelengths of light.

4. The oximetry system of claim 3, wherein said demodulator means comprises an amplitude demodulator.

5. The oximetry system of claim 1, further comprising:
    means for converting analog signals to digital signals, said converting means exhibiting a defined input dynamic range; and
    means, having an input responsive to electrical signals corresponding to said two wavelengths of light and an output coupled to the input of said converting means, for shifting the levels of said received signals to a significant portion of said input dynamic range of said converting means.

6. The oximetry system of claim 5, wherein said shifting means includes an offset voltage source and a capacitor which is selectively charged by said offset voltage source to shift said electrical signals.

7. The oximetry system of claim 5, wherein said converting means is further coupled to receive said electrical signals corresponding to said two wavelengths of light which have not been level-shifted.

8. The oximetry system of claim 1, wherein said measuring means is responsive to successive signals for detecting the signal peak at the transition from diastole to systole.

9. The oximetry system of claim 8, wherein said measuring means is further responsive to successive signals for detecting the minimum signal level at the end of systole.

10. The oximetry system of claim 9, wherein said integrating means is initialized in response to the detection of said signal peak by said measuring means, and integration of said signal waveform ends upon detection of said minimum signal level by said measuring means.

11. The oximetry system of claim 10, further including means, responsive to said measuring means, for storing the values of said detected signal peaks.

12. The oximetry system of claim 11, wherein said combining means produces a quotient by dividing said integral values by said signal peak values.

13. The oximetry system of claim 12, wherein said combining means produces a first quotient corresponding to one of said wavelengths of light and a second quotient corresponding to the other of said wavelengths of light.

14. The oximetry system of claim 13, wherein said combining means produces an index value by dividing said first quotient by said second quotient.

15. The oximetry system of claim 14, wherein one of said wavelengths of light is in the infrared region and the other of said wavelengths of light is in the red region, said first quotient corresponds to infrared light signals and said second quotient corresponds to red light signals.

16. The oximetry system of claim 14, wherein said means responsive to said index values comprises a look-up table.

17. The oximetry system of claim 10, wherein said electrical signal producing means includes
   means for shifting the levels of said electrical signals corresponding to said two wavelengths of light; and
   means for producing digitized samples of said shifted received signals and of received signals which have not been shifted;
   wherein said measuring means is responsive to received signals which have not been shifted and said integrating means is responsive to said shifted received signals.

18. The oximetry system of claim 5, wherein said shifting means is selectively operable during the diastolic interval.

* * * * *